(12) United States Patent
Lazar et al.

(10) Patent No.: US 6,277,579 B1
(45) Date of Patent: *Aug. 21, 2001

(54) DIRECT DETECTION OF RNA MEDIATED BY REVERSE TRANSCRIPTASE LACKING RNASE H FUNCTION

(75) Inventors: James G. Lazar, Bethesda; Abel De La Rosa, Gaithersberg; Clayton D. Collier, Germantown, all of MD (US)

(73) Assignee: Digene Corporation, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/440,419

(22) Filed: Nov. 15, 1999

Related U.S. Application Data

(63) Continuation-in-part of application No. 09/020,067, filed on Feb. 6, 1998, now Pat. No. 5,994,079.

(51) Int. Cl.$^7$ ............................. C12Q 1/68; G01N 33/53; C12P 19/34; C07K 16/00; C12N 15/11

(52) U.S. Cl. ............................. 435/6; 435/7.1; 435/91.1; 530/388.1; 536/23.1

(58) Field of Search ................................ 435/6, 91.1, 7.1; 436/501; 536/23.1, 24.3, 24.33; 530/388.1

(56) References Cited

U.S. PATENT DOCUMENTS

| | | | |
|---|---|---|---|
| 4,563,417 | 1/1986 | Albarella et al. | 435/6 |
| 4,732,847 | 3/1988 | Stuart et al. | 435/6 |
| 4,743,535 | 5/1988 | Carrico | 435/6 |
| 4,833,084 | 5/1989 | Carrico | 435/240.27 |
| 5,412,087 | 5/1995 | McGall et al. | 536/24.3 |
| 5,429,807 | 7/1995 | Matson et al. | 442/131 |
| 5,455,170 | 10/1995 | Abramson et al. | 435/252.3 |
| 5,510,270 | 4/1996 | Fodor et al. | 536/518 |
| 5,668,005 | 9/1997 | Kotewicz et al. | 435/194 |

FOREIGN PATENT DOCUMENTS

| | | |
|---|---|---|
| 480 289 | 10/1991 | (EP) . |
| 2279954 | 1/1995 | (GB) . |
| WO93/10263 | 5/1993 | (WO) . |
| WO96/24694 | 8/1996 | (WO) . |
| WO97/10364 | 3/1997 | (WO) . |

OTHER PUBLICATIONS

Boguslawski, et al., "Characterization of monoclonal antibody to DNA—RNA and its application to immunodetection of hybrids," *J. Immunol. Methods* 89:123–130 (1986).

Coutlee, et al., "Comparison of Colorimetric, Fluorescent, and Enzymatic Amplification Substrate Systems in an Enzyme Immunoassay for Detection of DNA–RNA Hybrids," *J. Clin. Microbiol.* 27(5): 1002–1007 (1989).

Grunstein, et al., "Colony hybridization: A method for the isolation of cloned DNAs that contain a specific gene," *Proc. Natl. Acad. Sci. USA* 72(10):3961–3965 (1975).

Guo, et al., "Direct fluorescence analysis of genetic polymorphisms by hybridization with oligonucleotide arrays on glass supports," *Nucleic Acids Res.* 22(24):5456–5465 (1994).

Hames & Higgins, *Nucleic Acid Hybridisation: A Practical Approach* (IRL Press Limited, Oxford, England. 1985).

Hermanson, et al., eds. *Immobilized Affinity Ligands* (Academic Press, New York, 1992).

Ishikawa, et al., "Enzyme–Labeling of Antibodies and their Fragments for Enzyme Immunoassay and Immunohistochemical Staining," *J. Immunoassay* 4(3): 209–327 (1983).

Itakura, et al., "Synthesis and Use of Synthetic Oligonucleotides," *Ann. Rev. Biochem.* 53:323–356 (1984).

Johnstone, et al., *Immunochemistry In Practice*, pp. 209–216 and 241–242 (Blackwell Scientific Publications, Oxford, England, 1987).

Khrapko, et al., "Hybridization of DNA with Oligonucleotides Immobilized in Gel: A Convenient Method for Detecting Single Base Substitutions," Mol Biol (Mosk) (USSR) 25(3):718–730 (translation page No. 581–591) (1991).

Kitawaga, et al., "Comparison of Poly(A)–Poly(dT)and Poly(I)–Poly(dC) as Immunogens for the Induction of Antibodies to RNA–DNA Hybrids," *Mol. Immunology* 19(3):413–420 (1982).

(List continued on next page.)

*Primary Examiner*—John S. Brusca
(74) *Attorney, Agent, or Firm*—Holland & Knight LLP

(57) ABSTRACT

Disclosed is a method of detecting RNA molecules of interest in which reverse transcription primers unique to the RNA molecule of interest are used for reverse transcribing the RNA with a reverse transcriptase lacking RNAse H function and the resulting RNA/DNA hybrid is detected with an antibody specific for RNA/DNA hybrids. The primers are immobilized on a solid support in order to associate the RNA/DNA hybrid with the solid support. This allows easy separation of hybrids form sample solution and specific detection of RNA molecules based on the position of the hybrid on the solid support. This method can be used to detect the presence of one or many specific RNA molecules which may be present in a sample, including RNA from different organisms (such as viruses, bacteria, fungi, plants, and animals), or RNA indicative of an infection, a disease state, or predisposition to a disease in an animal. The specificity of detection is increased relative to current detection methods involving probe hybridization since the reverse transcription primers are shorter and less subject to non-specific hybridization. Specificity of the disclosed method can also be increased by using a thermostable reverse transcriptase and performing reverse transcription at a high temperature. The disclosed method can also be used to detect reverse transcriptase activity in a sample and to identify inhibitors of reverse transcriptase. Also disclosed is a method for sequencing target RNA molecules using reverse transcriptase lacking an RNAse H function.

28 Claims, No Drawings

OTHER PUBLICATIONS

Lesnick, et al., "Relative Thermodynamic Stability of DNA, RNA, and DNA–RNA Hybrid Duplexes: Relationship with Base Composition and Structure," *Biochemistry* 34:10807–10815 (1995).

*Maniatis, et al., Molecular Cloning: A Laboratory Manual (New York, Cold Spring Harbor Laboratory, 1982).

*Maskos et al., "Oligonucleotide hybridizations on glass supports: a novel linker for oligonucleotides synthesized in situ," *Nucleic Acids Research* 20:1679–1684 (1992).

McGraw et al., "Sequence–Dependent Oligonucleotide–Target Duplex Stabilities: Rules from Empirical Studies with a Set of Twenty–Mers," *Biotechniques* 8(6):674–678 (1990).

Means, et al, "Chemical Modifications of Proteins: History and Applications," *Bioconj. Chem.* 1:2–12 (1990).

Mierendorf, et al., "Sequencing of RNA Transcripts Synthesized in Vitro from Plasmids Containing Bacteriophage Promoters," *Methods Enzymol.* 152:563–566 (1987).

Narang, et al., "Chemical Synthesis of Deoxyoligonucleotides by the Modified Triester Method," *Methods Enzymol.* vol. 65, Chapter 61, pp. 610–620 (1980).

Pease, et al., "Light–generated oligonucleotide arrays for rapid DNA sequence analysis," *Proc. Natl. Acad. Sci. USA* 91(11):5022–5026 (1994).

Rychlik, et al., "Optimization of the annealing temperature for DNA amplification in vitro," *Nucleic Acids Res.* 18(21):6409–6412 (1990).

*Sambrook et al., *Molecular Cloning*: A Laboratory Manual, 2nd Edition (Cold Spring Harbor Laboratory Press, Cold Spring Harbor, N.Y., 1989) Chapters 5, 6).

Schena, et al., "Quantitative Monitoring of Gene Expression Patterns with a Complementary DNA Microarray," *Science* 270:467–470 (1995).

Southern, "Detection of Specific Sequences Among DNA Fragments Separated by Gel Electrophoresis," *J. Mol. Biol.* 98(1):503–517 (1975).

Stimpson, et al., "Real–time detection of DNA hybridization and melting on oligonucleotide arrays by using optical wave guides," *Proc. Natl. Acad. Sci. USA* 92:6379–6383 (1995).

Stuart, et al., "Location of the 18/28S ribosomal RNA genes in two Hawaiian *Drosophila* species by monoclonal immunological identification of RNA–DNA hybrids in situ," *Proc. Natl. Acad. Sci. USA* 78(6):3751–3754 (1981).

Syvänen, et al., "Fast quantification of nucleic acid hybrids by affinity–based hybrid collection," *Nucleic Acids Res.* 14(12):5037–5048 (1986).

Taylor, ed. *Protein immobilization: fundamentals and applications*, (M. Dekker, New York, 1991).

DIRECT DETECTION OF RNA MEDIATED BY REVERSE TRANSCRIPTASE LACKING RNASE H FUNCTION

CROSS-REFERENCE TO RELATED APPLICATIONS

This application is a continuation-in-part of application Ser. No. 09/020,067, filed Feb. 6, 1998, U.S. Pat. No. 5,994,079, entitled "Direct Detection of RNA Mediated by Reverse Transcriptase Lacking RNase H Function," by Abel De La Rosa and Clayton D. Collier. application Ser. No. 09/020,067, filed Feb. 6, 1998, is hereby incorporated herein by reference.

FIELD OF THE INVENTION

The present invention is in the general field of detection of nucleic acid sequences, and specifically in the field of detection of specific RNA sequences.

BACKGROUND OF THE INVENTION

The RNA or DNA for many genes, including those associated with disease states, and microorganisms and viruses have been isolated and sequenced. Nucleic acid probes based on such sequences are currently available to identify a large number of genes and infections. Nucleic acid probes are detectable nucleic acid sequences that hybridize to complementary RNA or DNA sequences in a test sample. Detection of the probe indicates the presence of a particular nucleic acid sequence in the test sample for which the probe is specific. In addition to aiding scientific research, DNA or RNA probes can be used to detect the presence of viruses and microorganisms such as bacteria, yeast and protozoa as well as genetic mutations linked to specific disorders in patient samples.

Grunstein, et al., *Proc. Natl. Acad. Sci. USA* 72:3961 (1975) and Southern, *J Mol. Biol.* 98:503 (1975) describe hybridization techniques using radiolabelled nucleic acid probes. Nucleic acid hybridization probes have the advantages of high sensitivity and specificity over other detection methods and do not require a viable organism. Hybridization probes are often labelled with a radioactive substance that can be easily detected.

Probes have been indirectly labelled in an attempt to avoid the problems associated with direct radioactive labelling. The most common method of indirect labelling is to attach biotin, a small vitamin, to the nucleic acid probe using a chemical or enzyme technique. Following hybridization to the specific RNA, the biotin is detected by reaction with streptavidin, a protein which binds biotin tightly and has been labelled with an enzyme or fluorochrome. Bound biotin-streptavidin complex can be detected by reaction with color-producing substrates and the fluorochrome can be seen when reacted with incident light of appropriate wavelength. However, indirect labelling of hybridization probes with biotin or other haptens often increases the "hydrophobicity" of the probe. The probe tends to interact non-specifically with materials other than the complementary nucleic acid target, leading to high background. High background reduces sensitivity and increases the likelihood of a false-positive result. Indirect labelling is also less sensitive than direct labelling because the labelling density is limited; only a small fraction of the bases are labelled giving a limiting number of sites for signal generation. An increase in the labelling density of a probe leads to increased non-specific binding, higher background, and ultimately, failure of the probe to hybridize with its target due to the interference of the hapten with base pairing. Indirectly labelled probes are therefore not well suited to clinical diagnosis.

Hybridization of a probe to the specific RNA sequences has been detected with the use of an intercalating agent such as acridine orange or ethidium bromide as described in U.S. Pat. No. 4,563,417 to Albarella et al. The intercalating agent becomes inserted between hybridized base pairs of probe and sample nucleic acids and causes the tertiary structure of the helix to unwind. An antibody specific for the newly formed antigenic determinant created by the intercalating agent and the unwound helix is detected by conventional means. This method lacks selectivity for the target hybrids because intercalating agents fail to recognize specific sequences. Furthermore, the antibodies recognize only the intercalating agent/nucleic acid complex, but do not detect a specific sequence. Therefore, additional selection or purification steps are required to prevent non-specific signal, making this approach poorly suited for clinical diagnosis.

Hybridization of the probe to the specific RNA sequences can also be detected with the aid of an antibody specific for a labelled probe as described in U.S. Pat. No. 4,743,535 to Carrico. The probe is labelled with a detectable substance such as flavin adenine dinucleotide (FAD) or a fluorescent agent. An antibody specific for the labelled probe, after it has hybridized to the specific RNA sequence, is detected by a biochemical reaction. This method of detection also creates non-specific binding and the likelihood of false-positive results and is not well suited for clinical screening.

Monoclonal antibodies to DNA-RNA hybrids are now available. U.S. Pat. No. 4,732,847 to Stuart et al. and the publication of Stuart et al., *Proc. Natl. Acad. Sci. USA* 78:3751 (1981) describe a method of hybridization detection of specific nucleic acid sequences on a solid surface involving a monoclonal antibody specific for a poly(A)-poly(dT) duplex. In Stuart, DNA/RNA hybrids are formed by annealing DNA or RNA sequences complementary to the sequence of interest.

A monoclonal antibody specific for DNA-RNA hybrids secreted by hybridoma HB 8730, is disclosed in U.S. Pat. No. 4,833,084 to Carrico et al. In Carrico, DNA/RNA hybrids are formed by annealing of RNA and DNA polynucleotides, or by transcription of DNA.

The isolation of anti-DNA-RNA hybridomas has improved the development of assays for genetic mutations linked to specific defects and the detection of bacterial and viral infections. However, assays utilizing these anti-hybrid monoclonal antibodies secreted from the hybridomas often employ large probes leading to a high level of non-specific binding causing false positive results. Boguslawski et al., *J Immunol. Methods* 89:123–130 (1986) developed a hybridization assay using anti-hybrid coated polystyrene beads isolated on filter paper in an attempt to reduce non-specific binding and avoid complicated washing procedures.

Therefore, it would be useful to have a method to detect RNA sequences that is easy to use, highly specific, accurate and sensitive enough for clinical screenings.

Accordingly, it is an object of the present invention to provide a method of detecting specific RNA molecules in a sample with a relatively large signal based on specific hybridization of a relatively small oligonucleotide primer.

It is further an object of the present invention to provide an assay having minimal false positives.

It is further an object of the invention to provide an assay to detect RNA indicative of an infection, a disease state, or predisposition to a disease.

It is further an object of the invention to provide an assay for detecting reverse transcriptase activity and testing for reverse transcriptase inhibitors.

BRIEF SUMMARY OF THE INVENTION

Disclosed is a method of detecting RNA molecules of interest in which reverse transcription primers unique to the RNA molecule of interest are used for reverse transcribing the RNA with a reverse transcriptase lacking RNAse H function and the resulting RNA/DNA hybrid is detected with an antibody specific for RNA/DNA hybrids. The primers are immobilized on a solid support in order to associate the RNA/DNA hybrid with the solid support. This allows easy separation of hybrids form sample solution and specific detection of RNA molecules based on the position of the hybrid on the solid support. This method can be used to detect the presence of one or many specific RNA molecules which may be present in a sample, including RNA from different organisms (such as viruses, bacteria, fungi, plants, and animals), or RNA indicative of an infection, a disease state, or predisposition to a disease in an animal. The specificity of detection is increased relative to current detection methods involving probe hybridization since the reverse transcription primers are shorter and less subject to non-specific hybridization. Specificity of the disclosed method can also be increased by using a thermostable reverse transcriptase and performing reverse transcription at a high temperature.

The disclosed method can be used to detect the presence of one or many specific RNA molecules which may be present in a sample. The method can be used to detect, for example, continuous amplification reaction (CAR) generated RNA (Anthony et al., Cambridge Healthtech Institute's Second Annual Gene Quantification Meeting; Abstract #2 (1997)), RNA from different organisms (such as viruses, bacteria, fungi, plants, and animals), or RNA indicative of an infection, a disease state, or predisposition to a disease. For example, mRNA specific to tumor cells can be detected. The method is also useful for detecting a class of microorganisms or a group of related disease conditions.

The disclosed method allows easy detection of a relatively large signal based on specific hybridization of a relatively small primer. The specificity of detection is increased relative to detection methods involving probe hybridization because the reverse transcription primers employed in the disclosed method are shorter and are therefore less subject to non-specific hybridization. The specificity of the disclosed method can be increased by using a thermostable reverse transcriptase and performing reverse transcription at a high temperature, such as a temperature around the melting temperature of the hybrid between the primer and target RNA. The sensitivity of the disclosed method can also be increased by treating the sample with a single-strand-dependent ribonuclease, such as RNAse A, following reverse transcription to remove free RNA present in the sample.

The disclosed method also be used to detect reverse transcriptase activity in a sample. A preferred use of this form of the method is the screening and testing for reverse transcriptase inhibitors against organisms harboring this enzyme (such as HIV), even if the reverse transcriptase has an RNase H function. For example, a target RNA can be hybridized to appropriate immobilized oligodeoxyribonucleotide primers, reverse transcribed in the presence of chain terminating dideoxynucleotides and the presumptive enzyme inhibitor. The chain terminated RNA:DNA hybrids can then be treated with RNase A (to digest unhybridized RNA portions of the duplex) and detected with an RNA/DNA hybrid-specific antibody. Detection of hybrids is indicative of enzyme activity and lack of inhibition. The amount of hybrid present can also be used to estimate the level of inhibition.

DETAILED DESCRIPTION OF THE INVENTION

Disclosed is a method of detecting RNA sequences by reverse transcribing all or part of the target RNA molecule with a reverse transcriptase lacking an RNA/DNA hybrid-dependent exonuclease function (commonly referred to as an RNAse H function or component) and detecting the resulting RNA/DNA hybrid with an antibody specific for RNA/DNA hybrids. The primers are immobilized on a solid support in order to associate the RNA/DNA hybrid with the solid support. This allows easy separation of hybrids form sample solution and specific detection of RNA molecules based on the position of the hybrid on the solid support.

Arrays of DNA strands on silicon chips, glass slides, or other solid substrates are in widespread use for measurement of gene expression (RNA). Several methods are available for preparing DNA arrays. Oligonucleotides or cDNA strands may be covalently bound to a solid substrate through chemical coupling methods. Other approaches utilize synthetic methods to build the oligonucleotide directly on the surface of the substrate. A simpler but more limited approach is to prepared labeled DNA and then bind the labeled DNA to a substrate that has been coated with a binding partner.

The DNA array has emerged as a preferred format for the miniaturization of assays that detect and measure gene expression. DNA arrays allow the expression of tens to thousands of genes to be measured from a single sample on a single device. A weakness of the traditional array methods is that the RNA to be measured must first be labeled, often through conversion of the RNA to labeled DNA, so that it can be detected and measured. The RNA labeling methods are expensive, time-consuming and may change the relative amounts of specific mRNA in sample due to sequence-specific differential labeling efficiency.

In the disclosed method, an antibody specific for RNA:DNA hybrids is utilized to detect RNA that has hybridized to the DNA array rendering the labeling of the RNA no longer necessary. In this approach, the longer the RNA:DNA hybrid, the greater the signal since a longer RNA:DNA hybrid can bind more antibody than a short RNA:DNA hybrid. Therefore, the longer the DNA strands on the array, the more sensitive the detection of RNA or alternative, the greater the signal intensity for a given amount of hybridized RNA. Unfortunately, it becomes more difficult and increasingly expensive to synthesize, prepare or utilize longer strands of DNA in the preparation of DNA arrays. In the disclosed assay described, relatively short oligonucleotide primer sequences are bound to the solid substrate, minimizing the time, effort, and expense necessary to create the array. RNA in the sample is hybridized to these short primers creating a short RNA:DNA hybrid with a long RNA tail (the average length of mRNA is about 1500 bases). This short RNA:DNA hybrid could probably only bind 1 or 2 anti-RNA:DNA antibodies. When reverse transcriptase is added, and conditions are such that reverse transcription occurs, the DNA portion of the RNA:DNA hybrid is extended to the length of the RNA strand, thus greatly increasing the length of the RNA:DNA hybrid. If the RNA strand were 1500 bases in length, then the resulting RNA:DNA hybrid would approach 1500 base pairs. An RNA:DNA hybrid of this length would bind significantly more anti-RNA:DNA antibody, thus greatly increasing the intensity of the signal produced, and increasing the sensitivity of detection of specific RNA sequences A preferred form of the disclosed method involves the following steps:

1. Prepare a primer or array of primers bound to a solid substrate (plates, slides, dishes, beads, particles, cups, strands, chips, and strips, both porous and non-porous) by, for example, one of the following methods:
   a. Use a labeled primer (such as biotin), and bind it to a solid phase that is pre-bound with a binding partner such as streptavidin.
   b. Binding the primer covalently to a solid phase through standard chemical techniques.
   c. The primer is synthesized directly on the solid phase through traditional DNA synthesis methods or through a light-directed chemical synthesis process, which combines solid-phase chemical synthesis with photolithographic fabrication techniques employed in the semiconductor industry (Affymetrix method).
2. Adding the sample containing the RNA of interest to the immobilized DNA primers and allowing RNA:DNA hybrids to form (these hybrids will be relatively short and will have long unhybridized RNA tails).
3. Add reverse transcriptase lacking RNAse H function.
4. Incubate under conditions that promote reverse transcription, thus forming a much longer RNA:DNA hybrid.
5. Optionally adding a single-strand specific ribonuclease, such as RNAse A, to degrade all remaining single-stranded RNA.
6. Adding an antibody specific for RNA:DNA hybrids.
7. Detecting the antibody bound to the immobilized RNA:DNA hybrids.

The disclosed method also allows easy detection of reverse transcriptase activity. This can be useful in the screening and testing for reverse transcriptase inhibitors against organisms harboring this enzyme (such as HIV), even if the reverse transcriptase has an RNAse H function. For example, a target RNA can be hybridized to appropriate immobilized oligodeoxyribonucleotide primers, reverse transcribed in the presence of chain terminating dideoxynucleotides and the presumptive enzyme inhibitor. The chain terminated RNA:DNA hybrids can then be treated with RNaseA (to digest unhybridized RNA portions of the duplex) and detected with an antibody specific for RNA/DNA hybrids. Detection of hybrids is indicative of enzyme activity and lack of inhibition. The amount of hybrid present can also be used to estimate the level of inhibition.

1. RNA Molecules of Interest

The disclosed method can be used to detect or sequence any RNA molecule or combination of RNA molecules in a sample. RNA molecules for detection, referred to herein as RNA molecules of interest, or target RNA molecules, are selected based on the needs and purpose of the detection. In general, an RNA molecule of interest can be chosen based on known criteria for selecting a nucleic acid sequence for detection. For example, a particular RNA molecule may be associated with a pathogen, a disease state, or a predisposition to a disease, and detection of such an RNA molecule can have a diagnostic value. For example, mRNA specific to tumor cells or normal cells can be detected.

The disclosed method can also be used to determine the ratio of expression of different RNA species from individual organisms or an individual sample. For this purpose, the method is used to detect multiple RNA species simultaneously. Array detection as disclosed herein is useful for this purpose. The disclosed method can also be used to detect similar or related RNAs where the related RNAs have a common sequence motif between them, but which are otherwise different. For example, cells may contain multiple RNA species having similar regulatory sequences, similar structural motifs, or other sequences in common. Such classes of RNA molecules can be detected with a single primer species by designing the primer to hybridize to the common sequence.

The disclosed method can also be used to detect a plurality of different RNA molecules of interest in a sample from an individual organism. This is preferably accomplished by either screening for an RNA sequence that is present in each of the RNA molecules of interest, or by screening with multiple primers that are collectively complementary to regions on the RNA molecules of interest. The later approach is preferred for use in detecting, for example, some diseases or predispositions to disease that are associated with numerous different mutations to particular genes. In this case, it is preferred to screen for sequences that are complementary to the regions of the mutant RNA products of these genes that are characteristic of each of the mutations.

The disclosed method also allows the detection of the RNA of interest in different organisms, such as, fungus, bacteria, plants, animals and viruses by taking samples from each of the organisms of interest. The disclosed method also allows the detection of CAR generated RNA molecules.

Another RNA molecule of interest may be associated with a class of microorganisms or a group of related disease conditions. For this purpose, RNA molecules can be chosen based on their common presence in all or most of the members of such groups. For example, to detect mycobacteria, it is preferred to select an RNA molecule that is both unique to mycobacteria and present in most types of mycobacteria. The identification and selection of nucleic acid molecules for detection is a well developed area and such identification and selection criteria can be fully applied to the identification and selection of RNA molecules as targets of detection in the disclosed method.

RNA molecules of interest for use in the disclosed method can come from various sources, both natural or synthetic. Various types of RNA include messenger RNA, ribosomal RNA, nucleolar RNA, transfer RNA, viral RNA and heterogeneous nuclear RNA, or the like. In addition, whole naturally occurring entities or fragments thereof may be used. 2. Samples to Be Assayed for RNA Samples to be used in the method of the invention are from any source identified as containing, or expected to contain, RNA. Preferred samples are those suspected or expected to contain one or more RNA molecules of interest. Samples can be, for example, subjects of a screen to determine which samples contain particular RNA molecules of interest, a body fluid or extract from a patient or other animal suspected of being infected or suffering from a disease condition, or an environmental sample (for example, soil or water) suspected of harboring a particular organism.

Alternatively, a sample for the disclosed method of the invention can be from any source containing or suspected of containing nucleic acid, where the nucleic acid has been treated to produce at least some RNA from the nucleic acid. The source of nucleic acid can be in purified or non-purified form. Preferred types of samples, or sources of samples, that are suitable for use in the disclosed method are those samples already known or identified as samples suitable for use in other methods of nucleic acid detection. Many such samples are known. For example, the sample may be from an agricultural or food product, or may be a human or veterinary clinical specimen. In a preferred embodiment, the sample is a biological fluid such as plasma, serum, blood, urine, sputum or the like. The sample may contain bacteria, yeast, viruses and the cells or tissues of higher organisms such as plants or animals, suspected of harboring an RNA of interest. Methods for the extraction and/or purification of RNA have been described, for example, by Maniatis et al., Molecular Cloning: A Laboratory Manual (New York, Cold Spring Harbor Laboratory, 1982).

3. Primers

Once the RNA(s) of interest have been identified and the RNA sample(s) obtained, a primer is needed to begin the reverse transcription of the RNA molecule of interest as shown in FIG. 1. A primer of the disclosed method is an oligonucleotide having sequence complementary to a region on the RNA molecule of interest. As used herein, the complementary sequence of the primer is referred to as the "complementary portion". As used herein, the region on the RNA molecule of interest complementary to the primer is referred to as the "primer complement region". The primer complement region of an RNA molecule of interest can be any region of the RNA molecule of interest. It is preferred that the primer complement region of an RNA molecule be at some distance from the 5' end of the RNA molecule. This provides a longer region of RNA template between the site of primer hybridization and the end of the RNA molecule, thereby amplifying the amount of RNA/DNA hybrid to be detected.

In general, the primer complement region of an RNA molecule of interest is chosen based on known criteria for selecting an RNA sequence for detection. For example, to detect a particular RNA molecule from among other RNA molecules, it is preferred that the primer complement region is characteristic of, or unique to, the RNA molecule of interest. If it is desired that any of a class of RNA molecules be detected, it is preferred that the primer complement region is chosen to have a sequence that is the same or substantially the same in all of the RNA molecules of interest. Once a primer complement region is selected, the sequence of the primer is designed or chosen to be complementary to the chosen primer complement region of the molecule of interest. The nucleotide sequence of many RNA molecules are known. Any RNA molecule for which a sequence is known or for which a sequence can be derived can be detected using the disclosed method.

In the method of the invention the complementary portion of a primer has a length that supports specific and stable hybridization between the primer and the primer complement region. Generally a primer of the present invention comprises 10 to 100 nucleotides, but is preferably 15 to 30 nucleotides.

The primers are coupled to a solid support or substrate. Primers provided in this manner are known as "solid-state primers." A preferred form of solid-state primer is an array of primers. Such an array is a solid support to which multiple different primers have been coupled or adhered in an array, grid, or other organized pattern.

Substrates for use in solid-state primers include any solid material to which the primers can be coupled or adhered. This includes materials such as acrylamide, cellulose, nitrocellulose, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state primers can have any useful form including thin films or membranes, beads, bottles, dishes, slides, fibers, woven fibers, shaped polymers, particles, chips and microparticles. Preferred substrate forms for a solid-state primer are microtiter dishes, glass slides, and tagged beads.

Primers immobilized on a substrate allow formation of RNA/DNA 5 hybrids localized on the substrate. Such localization provides a convenient means of washing away reaction components that might interfere with subsequent detection steps, and a convenient way of assaying for multiple different RNAs simultaneously. Diagnostic RNA/DNA hybrids can be independently formed at each site where a different primer is adhered. For immobilization of primers to form a solid-state sample, the methods described below can be used.

A preferred form of solid-state primer is a glass slide to which up to 256 separate primers can be adhered as an array of small dots. Each dot is preferably from 0.01 to 2.5 mm in diameter, and most preferably around 0.25 mm in diameter. Such microarrays can be fabricated, for example, using the method described by Schena et al., Science 270:487–470 (1995). Briefly, microarrays can be fabricated on poly-L-lysine-coated microscope slides (Sigma) with an arraying machine fitted with one printing tip. The tip is loaded with 1 μl of a primer sample (0.5 mg/ml) from, for example, 96-well microtiter plates and deposited approximately 0.005 μl per slide on multiple slides at the desired spacing. The printed slides can then be rehydrated for 2 hours in a humid chamber, snap-dried at 100° C. for 1 minute, rinsed in 0.1% SDS, and treated with 0.05% succinic anhydride prepared in buffer consisting of 50% 1-methyl-2-pyrrolidinone and 50% boric acid. Microarray solid-state primers can scanned with, for example, a laser fluorescent scanner with a computer-controlled XY stage and a microscope objective. A mixed gas, multiline laser allows sequential excitation of multiple fluorophores.

In one embodiment primers for use in the disclosed method are synthesized using established oligonucleotide synthesis methods. Methods to produce or synthesize oligonucleotides are well known in the art. Such methods range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323–356 (1984), (phosphotriester and phosphite-triester methods), and Narang et al., Methods Enzymol., 65:610-620 (1980), (phosphotriester method).

Hybridization of the primer to the RNA molecule of interest can be carried out under any suitable conditions, and preferably under conditions which favor hybrid DNA complexing between RNA and DNA. See for example, Sambrook et al., *Molecular Cloning: A Laboratory Manual,* 2nd Edition (Cold Spring Harbor Laboratory Press, Cold Spring Harbor, N.Y., 1989).

4. Reverse Transcription

In the disclosed method, reverse transcription is carried out using a reverse transcriptase, preferably a reverse transcriptase lacking RNAse H function. The reaction mixture including the RNA molecule of interest, the hybridized immobilized primer, and the reverse transcriptase is then incubated under conditions to allow reverse transcription of the RNA molecule of interest and formation of DNA/RNA hybrids. Examples of reverse transcriptases that can be used in the disclosed method, or that can be adapted for use in the disclosed method are listed in Table 1. Preferred reverse transcriptases for use in the present method include reverse transcriptases 18053-017, 18064-014 and 18064-071 from Life Technology; reverse transcriptases M5301 and M5302 from Promega; and reverse transcriptase 600085 from Strategene; each disclosed in Table 1.

TABLE 1

| SPECIFIC ACTIVITY | UNITS DEFINITION | PREPARATION FORM | ADDITIONAL ACTIVITIES | SUPPLIER CATALOG NO. |
|---|---|---|---|---|
| | 1 unit incorporates 1 nmol TTP into acid-insoluble form/10 min at 35° C. using poly(A).oligo $dT_{12-28}$ as substrate | 0.2 M $KPO_4$, 2 mM DTT, 0.2% Triton X-100, 50% glycerol, pH 7.2 | No detectable RNase, exonuclease | Adv Biotech AB-0321 AB-0321b |
| 26,700 U/mL | 1 unit incorporates 1 nmol dTMP into acid-precipitable form/10 min at pH 8.3, 37° C. | 200 mM $KPO_4$, 2 mM DTT, 0.2% Triton X-100, 50% glycerol, pH 7.2 | No detectable endonuclease, RNase | ACS Heidelb F00750S F00750M |
| 10–20 U/μl | 1 unit incorporates 1.0 nmol [$^3$H]-JTTP into acid-insoluble products/10 min at 37° C. | 0.2 M $KPO_4$, 2.0 mM DTT, 0.2% Triton X-100, 50% glycerol, pH 7.2 | No detectable endonuclease, exonuclease, RNase | Amersham E 70041Y E 70041Z |
| >50,000 U/mg; >20,000 U/mL | 1 unit incorporates 1 nmol [$^3$H]-dTMP into acid-precipitable products/10 min at 37° C. using poly(A).d[pT]$_{15}$ as template primer | 200 mM $KPO_4$, 2 mM DTT, 0.2% Triton X-100, 50% glycerol, pH 7.2 | No detectable nonspecific RNases, nonspecific DNases (gel electrophoresis) | Boehringer 10911B 1495062 |
| 30,000 u/mL | 1 unit incorporates 1 nmol [$^3$H]-TMP into nucleic acid product/10 min at 37° C. | Solution containing 0.2 M $KPO_4$, 2.0 mM DTT, 0.2% Triton X-100, 50% glycerol, pH 7.2 | No detectable nonspecific nuclease | ICN 855928 855929 |
| 13 U/μL | 1 unit incorporates 1 nmol dTNP into a TCA-insoluble product/10 min at pH 8.3, 37° C. | 0.2 M $KPO_4$, 2 mM DTT, 0.2% Triton X-100, 50% glycerol, pH 7.2 | No detectable RNase, exogenous, nicking or degradation of RNA | NBL Gene 020704 |
| 30 U/μL | 1 unit incorporates 1 nmol dTNP into a TCA-insoluble product/10 min at pH 8.3, 37° C. | 0.2 M $KPO_4$, 2 mM DTT, 0.2% Triton X-100, 50% glycerol, pH 7.2; for high efficiency synthesis of full length cDNA in the 6–10 kilobase range | No detectable RNase, exonuclease, endonuclease, nicking | NBL Gene 020703 |
| >20,000 U/mg; 10,000–20,000 U/mL | 1 unit incorporates 1 nmol dNTP into DE-81 adsorbable form/10 min at 37° C. | 200 mM $KPO_4$, 2 mM DTT, 0.2% Triton X-100, 50% glycerol, pH 7.2 | No detectable RNase, DNase | Oncor 120111 120112 |
| 25,000–50,000 U/mg protein; 10,000–20,000 U/mL | 1 unit incorporates 1 nmol dTMP into acid-insoluble product/10 min at pH 8.3, 37° C. using poly(A)p[dT]$_{12-18}$ as template primer | Molecular biology grade; homogeneous purity; solution containing 0.2 M $KPO_4$, 2.0 mM DTT, 0.2% Triton X-100, 50% glycerol, pH 7.2 | No detectable RNase, DNase, nickase | Pharmacia 27-0922-01 27-0922-02 |
| 10,000–70,000 U/mL | 1 unit incorporates 1.0 nmol [$^3$H]-dTTP into acid-insoluble product/10 min at 37° C. | Purified; 20 mM $KPO_4$, 2 mM DTT, 0.2% Triton X-100, 50% glycerol, pH 7.2 | No detectable endonuclease, nonspecific RNase | Stratagene 600081 600082 |
| >40,000 U/mg; >20,000 U/mL | 1 unit incorporates 1 nmol TMP in acid-insoluble product/10 min at 37° C. with poly(A.[dT]$_{15}$ as substrate | Cooiassie Blue shows a single band purity; 50 mM Tris.HCl, 10 mM DTT, 100 mM NaCl, 0.05% polydoconal, 1 mM EDTA, 50% glycerol, pH 8.4 | No detectable nonspecific RNases, nonspecific DNases (gel electrophoresis) | Boehringer 1062603 |
| 50–250 U/μL | 1 unit incorporates 1 nmol deoxynucleotides into acid-precipitable material/10 min at 37° C. using poly(rA).oligo[dT]$_{12-18}$ as template primer | >90% purity by SDS-PAGE; 20 mM Tris.HCl, 0.1 M NaCl, 0.1 mM EDTA, 1 mM DTT, 0.01% NP40, 50% glycerol, pH 7.5 | No detectable non-specific ss- and ds-endonuclease, exonuclease, RNase | Amersham E 70456Y E 70456Z |
| 50,000 U/mL | 1 unit incorporates 1 nmol TTP into acid-insoluble form/10 min at pH 8.0, 37° C. using poly(rA).oligo[dT] as template primer | 50 mM Tris.HCl, 0.1 mM DTT, 100 mM NaCl, 1 mM EDTA, 0.1% NP40, 50% glycerol, pH 8.3 | No detectable endonuclease, RNase | ACS Heldelb F00755S F00755M |
| 200 U/μL | 1 unit incorporates 1 nmol deoxyribonucleotide into acid-precipitable material/10 min at pH 8.3, 37° C. using poly(A)-oligo.[dT]$_{12-18}$ as template primer | Purity by SDS-PAGE, 250 mM Tris.HCl, 15 mM $MgCl_2$, 375 mM KCl, pH 8.3 and 100 mM DTT | No detectable RNase H | Life Technol 18053-017 |
| 200 U/μL | 1 unit incorporates 1 nmol deoxyribonucleotide into acid-precipitable material/10 min at pH 8.3, 37° C. using poly(A)-oligo.[dT]$_{12-18}$ as template primer | Purity by SDS-PAGE, 250 mM Tris.HCl, 15 mM $MgCl_2$, 375 mM KCl, pH 8.3 and 100 mM DTT | No detectable RNase H | Life Technol 18064-014 18064-071 |
| 200 U/μL | 1 unit incorporates 1 nmol deoxyribonucleotide into acid-precipitable material/10 min at pH 8.3, 37° C. using poly(A)-oligo.[dT]$_{12-18}$ as template primer | | | Life Technol 28025-013 28025-021 |
| 25,000 U/mL | 1 unit incorporates 10 nmol TTP into acid-insoluble material/10 min at 37° C. using poly(rA).oligo(dT) as template primer | 0.1 mM NaCl, 50 mM Tris.Hcl, 5 mM DTT, 1 mM EDTA, 0.1% NP40, 50% glycerol, pH 7.6 | No detectable endonuclease, RNase | NE Biolabs 253S 253L |

TABLE 1-continued

| SPECIFIC ACTIVITY | UNITS DEFINITION | PREPARATION FORM | ADDITIONAL ACTIVITIES | SUPPLIER CATALOG NO. |
|---|---|---|---|---|
| ≧5000 U/mg protein | 1 unit incorporates 1.0 nmol [$^3$H]-TMP into acid-insoluble products/10 min at 37° C. using poly(A).d[pT]$^{15}$ as substrate | Recombinant; 99% by HPLC, SDS-PAGE; lyophilized containing 0.2% BSA as stabilizer | No detectable nuclease | Boehringer 1465333 |
| 20–40 U/μL | 1 unit incorporates 1 nmol deoxyribonucleotide into DE-81 absorbable form/10 min at 37° C. | Overproducer; 50 mM Tris.HCl, 0.1 M NaCl, 0.1% Triton X-100, 1 mM EDTA, 5 mM DTT, 50% glycerol, pH 8.3 | No detectable endo and exodeoxyribonucleases, RNases | Fermentas EP0351 EP0352 |
| 100–200 U/μL | 1 unit incorporates 1 nmol dTTP into acid-insoluble form/10 min at pH 8.3, 37° C. | Recombinant; ≧90% purity by SDS gel; 5X reaction buffer; 250 mM Tris.HCl, 375 mM KCl, 15 mM MgCl$_3$, 50 mM DTT, pH 8.3 | No detectable RNase H <1% DNase <3% RNase ≧90% supercoiled plasmid | Promega M5301 M5302 |
| | 1 unit incorporates 1 nmol TTP into acid-insoluble form/10 min at 37° C. using poly(A).oligo[dT]$_{11-18}$ as substrate | 50 mM Tris.HCl, 0.1 M NaCl, 1 mM EDTA, 5 mM DTT, 0.1% Triton X-100, 50% glycerol, pH 8.3 | No detectable RNase, exonuclease | Adv Biotech AB-0322 AB-0322b |
| | 1 unit incorporates 1 nmol dTTP into acid-insoluble form/10 min at 37° C. | 50 mM Tris.HCl, 5.0 mM DTT, 1.0 mM EDTA, 0.1 M NaCl, 0.1% NP40, 50% glycerol, pH 8.0 | No detectable endonuclease, RNase | CHIMBRx 1375-01 1375-02 |
| 35,000 U/mg | 1 unit incorporates 10 nmol dTTP into acid-insoluble material/10 min at pH 8.6, 37° C. using oligo.(dT)$_{12-18}$ primed poly(A)$_n$ as template | Solution containing 50% glycerol, 50 mM Tris.HCl, 0.1 M NaCl, 0.1 mM EDTA, 1 mM DTT, 0.1% Triton X-100, pH 7.5 | No detectable RNase, endonuclease, exonucleolytic DNase, protease | Epicentre M4425H M4410H |
| | 1 unit incorporates 1 nmol labeled dATP into acid-insoluble material/10 min at 37° C. | Solution containing 0.1 mM NaCl, 50 mM Tris.HCl, 1 mM EDTA, 5 mM DTT, 0.1% NP40, 50% glycerol, pH 8.0 | | ICN 152020 |
| | 1 unit incorporates 1 nmol TMP into DE-81 adsorbable form/10 min at 37° C. using polyA-oligodT$_{12-18}$ as substrate | 50 mM Tris.HCl, 0.1 M NaCl, 5 mM DTT, 1 mM EDTA, 0.1% Triton X-100, 50% glycerol, pH 8.3 | No detectable RNase, DNase | Oncor 120301 120302 |
| 50,000–95,000 U/mg protein; 10,000–20,000 U/mL | 1 unit incorporates 1 nmol dTMP into acid-insoluble product/10 min at pH 8.3, 37° C. using poly(rA).p[dT]$_{12-18}$ as template primer | Molecular biology grade; homogeneous purity; solution containing 50 mM Tris.HCl, 0.1 M NaCl, 1 mM EDTA, 5 mM DTT, 0.1% Triton X-100, 50% glycerol, pH 8.3 | No detectable RNase, DNase, nickase | Pharmacia 27-0925-01 27-0925-02 |
| 50,000 U/mL | 1 unit incorporates 1.0 nmol [$^3$H]TTP into acid-insoluble product/10 min at 37° C. | 50 mM Tris.HCl, 5 mM DTT, 1 mM EDTA, 100 mM NaCl, 0.1% NP40, 50% glycerol, pH 8.0 | No detectable RNase H, DNase, nonspecific RNase | Strategene 600085 |
| 10–30 U/uL | 1 unit incorporates 1 nmol [$^3$H]dTMP/10 min at 37° C. with poly(rA).oligo(dT) as template primer | 200 mM KPO$_4$, 2 mM DTT, 0.2% NP40, 50% glycerol, pH 7.2 | No detectable non-specific nuclease | Amersham E 2610Y E 2610Z |
| 400 U and 1600 U | 1 unit incorporates 1 nmol ($^3$H]dTMP/10 min at pH 8.3, 37° C. with poly(rA).oligo(dT) as template primer | Solution containing 200 mM KPO$_4$, 2 mM DTT, 0.2% NP40, 50% glycerol, pH 7.2 | No detectable nuclease | TaKaRa 2610 |
| | Transcriptase: 1 unit incorporates 4 nmol dTTP into acid insoluble material/30 min at pH 8.3, 45° C. using oligo(dT)18-primed poly(A)$_n$ as template; DNA Polymerase: 1 unit incorporates 10 nmol dNTP into acid insoluble material/30 min at pH 8.3, 74° C. | Solution containing 50% glycerol, 50 mM Tris.HCl, 0.1 M NaCl, 0.1 mM EDTA, 1 mM DTT, 0.5% Tween 20, 0.5% NP40, pH 7.5; no detectable DNA exo- and endonuclease, protease, RNase | | Epicentre Retrotherm ™ RT R19250 R19500 R1910H |
| | 1 unit incorporates 1 nmol dTTP into acid-insoluble form/10 min at 50° C. | 50 mM Tris.HCl, 5.0 mM DTT, 0.1 mM EDTA, 50% glycerol, stabilizers, pH 7.5 | No detectable endonuclease, 3'-exonuclease, 5'-exonuclease/5'-phosphatase, nonspecific RNase, ss- and ds-DNase | CHIMERx 1374-01 1374-02 |

Reverse transcription can generally be performed at any temperature within the functional temperature range of the reverse transcriptase. Preferably, the temperature of incubation is any temperature at which the reverse transcriptase is functional and the primer remains hybridized to the RNA molecule. For non-thermophilic reverse transcriptases, preferred temperatures are those temperatures that are at or around the optimum temperature for the reverse transcriptase. For most non-thermophilic reverse transcriptases this temperature will be between about 25° C. and 45° C.

In a preferred embodiment, a thermophilic reverse transcriptase is used for increasing selectivity. The highest temperature at which a thermophilic reverse transcriptase is functional can be quite high. For this reason, preferred temperature ranges for reverse transcription when a thermophilic reverse transcriptase is used are most conveniently described in terms of the calculated melting temperature of a hybrid between the RNA molecule of interest and the primer. Such a melting temperature is referred to herein as the RNA/primer melting temperature (R/P Tm). Preferred ranges include a temperature from 20° C. below the melting temperature of a hybrid between the RNA molecule of interest and the primer and 5° C. above the melting temperature of a hybrid between the RNA molecule of interest and the primer. Other preferred ranges when using a thermophilic reverse transcriptase include from 20° C. below R/P Tm to R/P Tm, from 15° C. below R/P Tm to R/P Tm, from 10C below R/P Tm to R/P Tm, from 7° C. below R/P Tm to RIP Tm, from 5C below R/P Tm to R/P Tm, from 3° C. below R/P Tm to R/P Tm, from 20° C. below R/P Tm to 5° C. below R/P Tm, from 15° C. below R/P Tm to 5° C. below R/P Tm, from 10° C. below R/P Tm to 5° C. below R/P Tm, from 7° C. below R/P Tm to 5° C. below R/P Tm, from 7° C. below RIP Tm to 3° C. below R/P Tm, and from 5° C. below R/P Tm to 3° C. below R/P Tm. It is specifically noted that every specific, but unnamed, range within the enumerated ranges above is contemplated as an alternative preferred range. Preferred temperatures for reverse transcription include about 20° C. below R/P Tm, about 15° C. below R/P Tm, about 12° C. below R/P Tm, about 10° C. below R/P Tm, about 7° C. below R/P Tm, about 5° C. below R/P Tm, about 3° C. below R/P Tm, 20° C. below R/P Tm, 15° C. below R/P Tm, 12° C. below R/P Tm, 10° C. below R/P Tm, 7° C. below R/P Tm, 5° C. below R/P Tm, and 3° C. below RIP Tm. In general, the closer the temperature is to the RIP Tm, the greater the degree of discrimination there will be between specific and non-specific hybrids of the RNA and primer. If the temperature is close to the R/P Tm, however, decreased stability of specific hybrids may cause priming to be less efficient.

R/P Tm can be determined either by calculation or by empirical measurement. For calculating R/P Tm, any established formula for calculating stability of nucleic acid hybrids can be used. A preferred formula for calculating RIP Tm is Tm=81.5+16.6 (log M)+0.41 (%G+C)−0.72 (% formamide), which was derived from studies on the stability of perfectly-matched DNA:DNA hybrids. For RNA:DNA hybrids, incorporating formamide concentration in the formula does not hold because the relationship between formamide concentration and the depression of Tm is not linear. At 80% formamide, RNA:DNA hybrids are more stable than DNA:DNA hybrids, increasing the Tm by about 10 to 30° C. depending on the sequence (Hames & Higgins, Nucleic Acid Hybridisation: A Practical Approach (IRL Press Limited, Oxford, England. 1985)). Carrying out the reaction in 80% formamide can therefore also be used to suppress formation of DNA:DNA duplexes, to preferentially select RNA:DNA hybrids, and to estimate the Tm for R/P. Because the empirically derived formulas for the estimation of RNA:DNA hybrid Tm may not be as accurate for short DNA primers, the hybridization temperature is preferably determined by assessing hybrid stability in 0.1–0.4 M monovalent cation at temperatures ranging from 40 to 60° C. R/P Tm can also be determined empirically (Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990)).

As used herein, a thermophilic reverse transcriptase is any reverse transcriptase that retains at least 5% of its maximum activity at any temperature above 50° C. or which has an optimal temperature of at least 50° C. Preferred reverse transcriptases are those which have an optimal temperature of at least 50° C. As used herein, maximum activity of a reverse transcriptase is defined as the activity, as measured in the assay described below, that a given reverse transcriptase exhibits at its optimal temperature. As used herein, optimal temperature of a reverse transcriptase is defined as the temperature at which the activity of the reverse transcriptase is greatest, as measured in the assay described below. The optimal temperature for a given reverse transcriptase can be determined by measuring its activity in the following assay at various temperatures. In general, an optimal temperature need be determined only to within a range so that assays need only be performed at intervals of 5 to 10 degrees.

5. Antibodies Specific for RNA/DNA Hybrids

As used herein, the term "antibody" is intended to include whole, intact antibodies, antibody fragments, polyfunctional antibody aggregates, or in general any antibody-derived substance that comprises at least one antibody combining site having the characteristics described herein. Antibodies of any of the known classes and subclasses of immunoglobulins are contemplated, for example, IgG, IgM, and so forth, as well as active fragments such as the IgG fragments conventionally known as Fab, F(ab'), and F(ab')$_2$.

A variety of particular techniques can be used to obtain suitable antibodies specific for RNA/DNA hybrids. See for example, the methods described in U.S. Pat. No. 4,833,084 to Carrico, U.S. Pat. No. 4,732,847 to Stuart et al. and the publication of Stuart et al., *Proc. Natl. Acad. Sci. USA* 78:3751 (1981), each of which is herein incorporated by reference.

Any anti-hybrid antibodies specific for a double-stranded RNA/DNA hybrids may be used to directly detect the hybrid of the invention. In a preferred embodiment of the present assay, a polyclonal anti-RNA/DNA hybrid antibody is derived from goats immunized with an RNA/DNA hybrid. Hybrid-specific antibody is purified from the goat serum by affinity purification against RNA/DNA hybrid immobilized on a solid support. Monoclonal antibody prepared using standard techniques can be used in place of the polyclonal antibodies.

The preferred antibody for RNA/DNA hybrids is prepared by the method of Kitawaga, Y. and Stollar, B. D., Mol. *Immunology* 19:413–420 (1982) or according to the method set forth in U.S. Pat. No. 4,732,847, issued Mar. 22, 1988 to Stuart et al., both of which are incorporated herein by reference.

Hybridized RNA-DNA samples are incubated with the antibodies for a sufficient amount of time to allow conjugation of the hybrids. The hybrids are bound to the antibodies by incubation for 5 minutes to 24 hours at 15 to 65° C. on a platform shaker with a shaking speed of 0 to 1500 rpm. Preferably, the incubation time is 30 to 120 minutes at 20 to 40° C., with shaking at 300 to 1200 rpm. Most preferably, binding occurs with incubation at one hour at room temperature with vigorous shaking on a rotary platform shaker with a rotary shaking speed between approximately 300 and 1000 rpm. It will be understood by those skilled in the art that the incubation time, temperature, and shaking can be varied to achieve alternative capture kinetics as desired.

6. Detection of Antibody-Hybrid Conjugate

The identification of the presence of the hybrids may now be achieved by employing monoclonal antibodies specific for the hybrid complex. Detection can be achieved by labeling either the monoclonal antibody specific for the hybrid DNA-RNA complex, or by employing labeled antibodies which bind to the anticomplex. For example, where the monoclonal antibody is derived from a mouse, antibodies to mouse antibodies, for example rabbit anti(-mouse IgG), could be labeled so as to bind to any anticomplex bound to the complex bound to the solid support.

A wide variety of labels have been used in other environments which would be applicable here. One of the more common labels is radionuclides, which can be used with autoradiography to visualize the areas of binding. Another label is a fluorescer such as fluorescein, mercocyanine, or rhodamine, which by irradiation with light of excitation, the presence of fluorescence can be monitored. Alternatively, an enzyme can be used which results in a product which can be detected and localized in the area of the enzyme. A large number of dyes or metals capable of reduction can be employed to provide detection. Common enzymes include horseradish peroxidase, glucose oxidase, β-galactosidase, alkaline phosphatase, or the like. The particular label or manner in which the detectable signal is observed is not critical to this invention. By employing antibodies to the anticomplex, the number of labels associated with a particular binding of the anticomplex to the complex can be greatly amplified.

In one embodiment the antibody conjugate is produced by well known means such as direct reduction of the monoclonal antibody with dithiothreitol, (DTT, Sigma Chemical Company, St. Louis, Mo.) to yield monovalent antibody fragments. The reduced antibody is then directly conjugated to maleimated alkaline phosphatase by the methods of Ishikawa et al., *J. Immunoassay* 4:209–237 (1983) and Means, G. and Feeney, R., *Bioconj. Chem.* 1: 2–12 (1990) and the resulting conjugate is purified by HPLC.

Alternatively, antibody-hybrid conjugate can be detected indirectly using an unlabelled anti-hybrid antibody for which a labelled antibody is specific. For example, the anti-hybrid antibody can be a mouse immunoglobulin that is detected by a labelled goat anti-mouse antibody. In addition, antibody- hybrid conjugates can be detected by conjugating the primer used for reverse transcription to a label, such as an enzyme, or to a hapten, such as biotin that is then detected with a labelled anti-hapten antibody. As described above, conjugated hybrid can also be detected with a direct labelled RNA probe, such as an enzyme-conjugated hybridization probe, or a hapten-modified probe that is subsequently detected by a labelled anti-hapten antibody.

Bound conjugate is subsequently detected by colorimetry or chemiluminescence as described by Coutlee, et al., *J. Clin. Microbiol.* 27:1002– 1007 (1989). Preferably, bound alkaline phosphatase conjugate is detected by chemiluminescence with a reagent such as a Lumi-Phos™ 530 reagent (Lumigen, Detroit, Mich.) using a detector such as an E/Lumina™ luminometer (Source Scientific Systems, Inc., Garden Grove, Calif.) or an Optocomp I™ Luminometer (MGM Instruments, Hamden, Conn.).

To facilitate detection of resulting binding of the antibody to the hybrid, the antibody will normally be labeled with a detectable chemical group. Examples of detectable chemical groups that can serve as labels are enzymatically active groups, such as coenzymes, enzyme substrates, enzyme inhibitors, and enzymes themselves, fluorescers, chromophores, luminescers, specifically bindable ligands such as biotin or haptens which are detectable by binding of labeled avidin or labeled anti-hapten antibodies, and radioisotopes.

7. Immobilization of Primers

Methods for immobilization of oligonucleotides to solid-state substrates are well established. Oligonucleotides, including half probes and rolling circle replication primers, can be coupled to substrates using established coupling methods. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

The immobilization and arraying of primer molecules to solid supports can be accomplished using any suitable technique. For example, immobilization can be accomplished either by in situ DNA synthesis (Maskos and Southern, *Nucleic Acids Research,* 20:1679–1684 (1992); Pease et al., *Proc. Natl Acad. Sci. USA,* 91:5022–5026 (1994)) or by covalent attachment of chemically synthesized oligonucleotides (Guo et al., *Nucleic Acids Research,* 22:5456–5465 (1994)) in combination with robotics arraying technologies. Other immobilization techniques are described in U.S. Pat. No. 5,412,087 to McGall et al., U.S. Pat. No. 5,429,807 to Matson et al., and U.S. Pat. No. 5,510,270 to Fodor et al. Thousands of different primers can be arrayed onto a small area on a solid support to interrogate thousands of target RNA molecules. The density of primers should be matched with the method of arraying and the means of detection.

Substrates for use in the disclosed method can include any solid material to which components of the assay can be adhered or coupled. Examples of substrates include, but are not limited to, materials such as acrylamide, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have any useful form including thin films or membranes, beads, bottles, dishes, fibers, woven fibers, shaped polymers, particles and microparticles. Preferred forms of substrates are plates and beads. The most preferred form of beads are magnetic beads.

A preferred form of array is a three dimensional array. A three dimensional array, as used herein, is a collection of tagged beads where each class of beads has a different tag associated with the bead. Each class of tagged bead then has a different primer attached. Thus, the tag on each bead identifies the specific primer attached to that bead. Use of the word tag is not intended to limit the nature of the tag. Tags can be any molecule, moiety, or characteristic that can be associated with a bead and that can be detected. Examples of useful tags are colors and transponders. Preferred tags are tags that can be detected by a signal (for example, color or electromagnetic field) rather than through interaction (such as ligand or hapten detection), although the later tags can be used. Useful tags for this purpose are available from Luminex (colored beads), Pharmaseq (transponder beads), and Illumina (colored beads).

Use of tagged beads allows multiple primers to be used simultaneously without the need for a surface array. Manipulations used in the disclosed method can also be simplified. For example, a mixture of tagged beads can be mixed with an RNA sample, followed by reverse transcription and association with anti-hybrid antibodies. By using either immobilized antibodies or by capturing the antibodies on a substrate, the beads on which DNA/RNA hybrids have formed can be separated from the beads where no hybrid has formed. The tags on the captured beads can then be detected and the identities of the primers determined. Many other assay schemes can be used for the disclosed method when using primers immobilized on tagged beads.

Primers can also be immobilized by using "capture tags." As used herein, a capture tag is any compound that can be associated with an oligonucleotide and which can bind to another compound or moiety. The primer is thus immobilized through binding of an attached capture tag to its binding partner. Such binding partners are referred to herein as "capture docks." Preferably, a capture tag is a compound, such as a ligand or hapten, that binds to or interacts with another compound, such as ligand-binding molecule or an antibody. It is also preferred that such interaction between the capture tag and the capture dock be a specific interaction, such as between a hapten and an antibody or a ligand and a ligand-binding molecule.

Suitable capture tags include hapten or ligand molecules that can be coupled to oligonucleotides. Preferred capture tags, described in the context of nucleic acid probes, have been described by Syvnen et al., *Nucleic Acids Res.,* 14:5037 (1986). Preferred capture tags include biotin, which can be incorporated into nucleic acids. The reverse transcription primer can be "captured," adhered to, or coupled to a substrate, that is, a solid support for the primer.

Adhering or coupling primers to a substrate may be accomplished by adhering or coupling capture docks to the substrate. The capture docks mediate adherence of a primer by binding to, or interacting with, a capture tag on the primer. Capture docks immobilized on a substrate allow capture of the primer on the substrate. By attaching different capture docks to different regions of a substrate different capture tags attached to different primers, can be captured at different, and therefore diagnostic, locations on the substrate. For example, in a microtiter plate multiplex assay, capture docks specific for up to 96 different capture tags can be immobilized on a microtiter plate, each in a different well. Capture and detection will occur only in those wells corresponding to capture tags for which the corresponding RNA molecules were present in a sample.

In one embodiment, the capture dock is an oligonucleotide. Methods for immobilizing and coupling oligonucleotides to substrates are well established. For example, attachment methods suitable for the present invention are described by Pease et al., *Proc. Nat. Acad. Sci. USA* 91(11) :5022–5026 (1994), and Khrapko et al., *Mol Biol (Mosk) (USSR)* 25:718–730 (1991). A method for immobilization of 3'-amine oligonucleotides on casein-coated slides, also suitable for the present invention, is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Methods for immobilizing proteins to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and Immobilized Affinity Ligands, Craig T. Hermanson et al., eds. (Academic Press, New York, 1992). Proteins can be attached to a substrate by chemically cross-linking a free amino group on the antibody to reactive side groups present within the substrate. For example, proteins may be chemically cross-linked to a substrate that contains free amino or carboxyl groups using glutaraldehyde or carbodiimides as cross-linker agents. In this method, aqueous solutions containing free proteins are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

8. RNAse A to Increase Sensitivity

In another embodiment, the sensitivity of the disclosed method is increased by treating the hybrid sample (following reverse transcription) with a single-strand-dependent ribonuclease, such as RNAse A, to remove free RNA present in the sample.

A solution preferably containing RNAse at a concentration between 0.01 and 1 mg/ml and the above described conjugated anti-hybrid molecule is incubated for approximately 5 minutes to 24 hours at temperature between 4 and 45° C. The purpose of the RNA digestion enzyme is to degrade non-specific free RNA that may be bound to the substrate. It is useful to remove the non-specific free RNA because secondary structures in the nucleic acid may be recognized by the detection means, resulting in elevated assay background. Preferably, the enzyme is added at a concentration between 0.05 and 0.5 mg/ml and is incubated for between 10 and 60 minutes. Most preferably, the enzyme is RNAse A (Sigma, St. Louis, Mo.) and is incubated with the conjugate for approximately 30 minutes at a concentration of 200 $\mu$g/ml. RNAse III (NCI, Frederick, Md.) can also be used.

The RNAse and conjugate are preferably diluted in a conjugation buffer that promotes specific antibody-antigen interaction, blocks non-specific binding of conjugate to the capture tube and stabilizes conjugate for long-term storage. A preferred buffer contains 0.1 M TrisTm-HCl, pH 7.5, 0.6 M NaCl to reduce cross reaction of antibody with other nucleic acid species, $ZnCl_2$ and $MgCl_2$ for stabilizing alkaline phosphatase, normal goat serum to block non-specific interaction of conjugate with the capture surface, 0.25% Tween™-20 to block non-specific binding of conjugate, and sodium azide as a preservative. A preferred wash buffer contains 0.1 M Tris™-HCI, pH 7.5, 0.6 M NaCl, 0.25% Tween™-20, and sodium azide as a preservative.

Detection of the antibody-hybrid conjugate is preferably achieved by binding the above-described labeled anti-hybrid molecule to the hybrid during the RNAse incubation. Tubes are then washed with the above-described wash buffer to remove any excess conjugate. Preferably, five manual washes are performed using either an Eppendorf™ Repeat Pipettor with a 50 ml Combitip™ (Eppendorf, Hamburg, Germany), a Corning™ repeat syringe (Coming, Coming, NY), a simple pump regulated by a variostat, or by gravity flow from a reservoir with attached tubing. Tube or plate washing systems for this use are commercially available.

9. RNA Detection Kit

RNA detection kits for use with the disclosed method can be made using some or all of the components required for the method. Preferably the kit contains at least a reverse transcriptase lacking RNA/DNA hybrid-dependent exonuclease function, immobilized or immobilizable primer, and an antibody specific for RNA/DNA hybrids. The kit preferably contains an immobilized primer that is complementary to a region on an RNA molecule of interest, and more preferably contains a plurality of immobilized primers that are each complementary to a region on an RNA molecule of interest.

The kit should contain a negative control and a positive control. Preferably, the negative and positive controls are included on the solid support with the primer.

10. Detection of Reverse Transcriptase Activity and Inhibitors

The disclosed method also allows easy detection of reverse transcriptase activity. This can be useful in the screening and testing for reverse transcriptase inhibitors against organisms harboring this enzyme (such as HIV), even if the reverse transcriptase has an RNase H function. A target RNA can be hybridized to appropriate immobilized oligodeoxyribonucleotide primers, reverse transcribed in the presence of chain terminating dideoxynucleotides and the presumptive enzyme inhibitor. The chain terminated RNA:DNA hybrids are then treated with RNase A (to digest unhybridized RNA portions of the duplex) and detected with the anti-hybrid antibody. Detection of hybrids is indicative of enzyme activity and lack of inhibition. The amount of hybrid present can also be used to estimate the level of inhibition.

The following non-limiting examples illustrate use of the present assay and kit.

Illustration

The following is an illustration of a preferred method of performing the disclosed method for the detection of a target RNA in a sample.

Mix 5' biotinylated 20 to 30 nucleotide primers with a streptavidin coated microtiter plate and capture for 30–60 minutes at 20–27° C. with constant shaking (1100 rpm). Add a sample of RNA to the plate. Add hybridization/extension buffer (100 mM Tris-HCl, pH 8.3, 150 mM KCl, 6 mM $MgCl_2$, 20 mM DTT and 1 mM each dNTP). Anneal the RNA and primer by heating the mixture to the optimal annealing temperature, preferably 60° C. (optimal annealing temperature varies with primer and RNA utilized), for 20–30 minutes. Cool the mixture at 20–27° C. for 10 minutes. Add an additional hybridization/extension buffer and RNase H- reverse transcriptase. Incubate the reaction for 30–60 minutes at 42° C. Add 0.5 M EDTA and 1.0 mg/ml RNase A. Incubate for 30 minutes at 37° C. Add anti-hybrid alkaline phosphatase conjugated antibody mix and incubate at 20–27° C. for 30–60 minutes. Wash the unbound antibody, and add a chemiluminescent substrate. Incubate for 15–30 minutes at 20–27° C. Read the signal utilizing a luminometer.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method for detecting RNA, the method comprising,
    (a) mixing an immobilized primer and a reverse transcriptase lacking RNA/DNA hybrid-dependent exonuclease function with a sample, wherein the primer is complementary to a region of an RNA molecule of interest in the sample,
    (b) incubating under conditions that promote reverse transcription, wherein an RNA/DNA hybrid is formed if the RNA molecule of interest is present in the sample, and wherein the RNA/DNA hybrid is a hybrid of the RNA molecule of interest and a reverse transcribed DNA molecule complementary to the RNA molecule of interest,
    (c) mixing an antibody specific for RNA/DNA hybrids with the sample, wherein the antibody binds to the RNA/DNA hybrid to form an antibody-RNA/DNA hybrid conjugate, and
    (d) detecting the antibody-RNA/DNA hybrid conjugate, wherein the presence of the antibody-RNA/DNA hybrid conjugate indicates the presence of the RNA molecule of interest in the sample.

2. The method of claim 1 wherein a plurality of immobilized primers are mixed with the sample, wherein each primer is complementary to a region of an RNA molecule of interest.

3. The method of claim 2 wherein each primer is complementary to a region of a different RNA molecule of interest.

4. The method of claim 1 wherein the method detects the presence of a plurality of RNA molecules of interest in a sample.

5. The method of claim 1 wherein the sample is obtained from an animal and wherein the presence of the RNA molecule of interest in the sample is indicative of an infection, a disease state, or predisposition to a disease in the animal.

6. The method of claim 5 wherein the method detects the presence of a plurality of RNA molecules of interest in a sample.

7. The method of claim 6 wherein detection of any one of the plurality of RNA molecules is indicative of an infection, a disease state, or predisposition to a disease in the animal.

8. The method of claim 1 wherein the primer is unique to the RNA molecule of interest.

9. The method of claim 1 wherein steps (a) and (b) are performed simultaneously.

10. The method of claim 1 wherein the primer is immobilized on a substrate.

11. The method of claim 10 wherein the substrate is selected from the group consisting of plates, slides, dishes, beads, particles, cups, strands, chips and strips.

12. The method of claim 11 wherein the substrate is selected from the group consisting of plates and magnetic beads.

13. The method of claim 1 wherein the reverse transcriptase is thermophilic.

14. The method of claim 13 wherein conditions that promote reverse transcription comprise a temperature from 20° C. below the melting temperature of a hybrid between the RNA molecule of interest and the primer to the melting temperature of a hybrid between the RNA molecule of interest and the primer.

15. The method of claim 14 wherein conditions that promote reverse transcription comprise a temperature from 5° C. below the melting temperature of a hybrid between the RNA molecule of interest and the primer to the melting temperature of a hybrid between the RNA molecule of interest and the primer.

16. The method of claim 1 wherein the primer comprises a capture tag, and wherein the primer is immobilized via the capture tag.

17. The method of claim 16 wherein the capture tag is biotin, wherein the primer is immobilized on a substrate, and wherein the substrate is coated with streptavidin.

18. The method of claim 16 wherein the capture tag is biotin.

19. The method of claim 1 further comprising labeling the antibody wherein the label is selected from the group comprising capture tags, fluorescers, radionuclides, and enzymes and wherein the method further comprises detecting the antibody.

20. The method of claim 1 further comprising a secondary antibody for specifically binding to the antibody, wherein the secondary antibody is labeled, the label being selected from the group comprising capture tags, fluorescers, radionuclides, and enzymes and wherein the method further comprises detecting the secondary antibody.

21. A method for detecting an RNA molecule of interest in a sample, the method comprising
   (a) mixing an immobilized primer and a reverse transcriptase lacking RNA/DNA hybrid-dependent exonuclease function with a sample, wherein the primer is complementary to a region of the RNA molecule of interest,
   (b) incubating under conditions that promote reverse transcription, wherein an RNA/DNA hybrid is formed if the RNA molecule of interest is present in the sample, and wherein the RNA/DNA hybrid is a hybrid of the RNA molecule of interest and a reverse transcribed DNA molecule complementary to the RNA molecule of interest,
   (c) mixing single-strand-dependent ribonuclease with the sample, wherein single-stranded RNA present in the sample is substantially degraded,
   (d) mixing an antibody specific for RNA/DNA hybrids with the sample, wherein the antibody binds to the RNA/DNA hybrid to form an antibody-RNA/DNA hybrid conjugate, and
   (e) detecting the antibody-RNA/DNA hybrid conjugate, wherein the presence of the antibody-RNA/DNA hybrid conjugate indicates the presence of the RNA molecule of interest in the sample.

22. The method of claim 21 wherein the single-strand-dependent ribonuclease is RNAse A.

23. A kit for detecting the presence of RNA sequences comprising
   (a) reverse transcriptase lacking RNA/DNA hybrid-dependent exonuclease function,
   (b) an immobilized primer that is complementary to a region on an RNA molecule of interest, and
   (c) an antibody specific for RNA/DNA hybrids.

24. The kit of claim 23 further comprising a plurality of primers that are each complementary to a region on an RNA molecule of interest.

25. A method for identifying inhibitors of reverse transcriptase, the method comprising incubating, in the presence and in the absence of a test compound, a reverse transcriptase lacking RNA/DNA hybrid-dependent exonuclease finction, an RNA molecule, and an immobilized primer under conditions that promote reverse transcription, and detecting any resulting RNA/DNA hybrid with an antibody specific for RNA/DNA hybrids, wherein if the amount of RNA/DNA hybrid detected in the presence of the test compound is less than the amount of RNA/DNA hybrid detected in the absence of the test compound then the test compound inhibits the reverse transcriptase.

26. A method for detecting reverse transcriptase activity in a sample, the method comprising incubating the sample in the presence of an RNA molecule and an immobilized primer under conditions that promote reverse transcription, and detecting any resulting RNA/DNA hybrid with an antibody specific for RNA/DNA hybrids.

27. The method of claim 26 wherein the method comprises
   (a) mixing the primer and the RNA molecule with the sample, wherein the primer is complementary to a region of the RNA molecule,
   (b) incubating under conditions that promote reverse transcription, wherein the RNA/DNA hybrid is formed if there is reverse transcriptase activity in the sample, and wherein the RNA/DNA hybrid is a hybrid of the RNA molecule and a reverse transcribed DNA molecule complementary to the RNA molecule,
   (c) mixing an antibody specific for RNA/DNA hybrids with the sample, wherein the antibody binds to the RNA/DNA hybrid to form an antibody-RNA/DNA hybrid conjugate, and
   (d) detecting the antibody-RNA/DNA hybrid conjugate, wherein the presence of the antibody-RNA/DNA hybrid conjugate indicates the presence of the reverse transcriptase activity in the sample.

28. The method of claim 26 further comprising incubating the sample in the presence of a test compound, wherein if the amount of RNA/DNA hybrid detected in the presence of the test compound is less than the amount of RNA/DNA hybrid detected in the absence of the test compound then the test compound inhibits the reverse transcriptase activity.

* * * * *